United States Patent
Klein et al.

(10) Patent No.: US 6,781,004 B2
(45) Date of Patent: Aug. 24, 2004

(54) PROCESS FOR THE PREPARATION OF CIS-6-HEXADECENOIC ACID

(75) Inventors: Daniela Klein, Mannheim (DE); Hansgeorg Ernst, Speyer (DE); Jürgen Koppenhöfer, Neustadt (DE)

(73) Assignee: BASF Aktiengesellschaft, Ludwigshafen (DE)

(*) Notice: Subject to any disclaimer, the term of this patent is extended or adjusted under 35 U.S.C. 154(b) by 34 days.

(21) Appl. No.: 10/061,316

(22) Filed: Feb. 4, 2002

(65) Prior Publication Data

US 2002/0107412 A1 Aug. 8, 2002

(30) Foreign Application Priority Data

Feb. 7, 2001 (DE) .......................... 101 05 799
Feb. 22, 2001 (DE) .......................... 101 08 603

(51) Int. Cl.$^7$ .............................. C07C 51/00
(52) U.S. Cl. ...................... 554/129; 554/128
(58) Field of Search ................. 554/128, 129

(56) References Cited

FOREIGN PATENT DOCUMENTS

| GB | 2 153 826 | 8/1985 |
| WO | 96/13591 | 5/1996 |
| WO | 98/16104 | 4/1998 |

OTHER PUBLICATIONS

Cravatt et al., JACOS, vol. 118, pp. 580–590, 1996.*
Gannett et al. "The Capsaicinoids: Their Separation, Synthesisa and Mutagenicity" J. Org. Chem. vol. 53 (1988) pp. 1064–1071.
Cravatt et al. "Structure Determination of an Endogenous Sleep Inducing Lipid cis–9–Octadecenamide (Olemide): A Synthetic Approach to the Chemical Analysis of Trace Quantities of a Natural Product" J. Am. Chem. Soc. (1996) vol. 118 pp. 580–590.

* cited by examiner

Primary Examiner—Deborah D. Carr
(74) Attorney, Agent, or Firm—Keil & Weinkauf

(57) ABSTRACT

The invention relates to a process for the preparation of cis-6-hexadecenoic acid of the formula I,

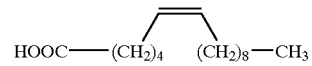

I which comprises reacting $a_1$) a triphenylphosphonium salt of the formula II, $$R^1OOC-(CH_2)_5-P(R^2)_3{}^+X^-$$ II with decanal of the formula III $$H_3C-(CH_2)_8-CH=O$$ III or $a_2$) a triphenylphosphonium salt of the formula IV, $$H_3C-(CH_2)_9-P(R^2)_3{}^+X^-$$ IV with an aldehyde of the formula V, $$R^1OOC-(CH_2)_4-CH=O$$ V in a Wittig reaction, and b) saponifying the ester, formed by process step $a_1$) or $a_2$), of the formula VI,

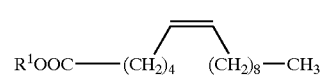

VI where the substituents $R^1$, $R^2$ and $X^-$ have the meanings given in the description.

5 Claims, No Drawings

PROCESS FOR THE PREPARATION OF CIS-6-HEXADECENOIC ACID

The invention relates to a process for the preparation of cis-6-hexadecenoic acid.

cis-6-Hexadecenoic acid (sapienic acid) is the most common unsaturated fatty acid present in human skin sebum. Because of its antimicrobial action, cis-6-hexadecenoic acid is a desired active ingredient for cosmetic and dermatological applications.

For the preparation of cis-6-hexadecenoic acid and esters thereof, microbiological and also chemical processes are known.

For example, WO 96/13591 describes the stereoselective elimination of hydrogen from palmityl esters by means of microorganisms.

A chemical synthesis route for obtaining cis-6-hexadecenoic acid is described in WO 98/16104. However, the multistage synthesis produces only small yields and, moreover, uses reagents which are questionable with regard to safety, such as, for example, liquid ammonia and potassium cyanide.

It is an object of the present invention to provide a novel process for the preparation of cis-6-hexadecenoic acid which proceeds with a high Z/E selectivity and does not have the disadvantages of the hitherto known processes with regard to safety.

We have found that this object is achieved by a process for the preparation of cis-6-hexadecenoic acid of the formula I

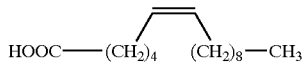

which comprises reacting a$_1$) a triphenylphosphonium salt of the formula II,

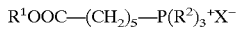

in which the substituents, independently of one another, have the following meanings:

R$^1$ is C$_1$–C$_{12}$-alkyl, aryl;
R$^2$ is aryl and
X$^-$ is an anion equivalent of an inorganic or organic acid with decanal of the formula III

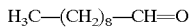

in a Wittig reaction, or reacting a$_2$) a triphenylphosphonium salt of the formula IV,

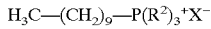

in which the substituents R$^2$ and X$^-$, independently of one another, have the meanings given above:
with an aldehyde of the formula V,

in which R$^1$ has the meaning given above,
in a Wittig reaction
and b) saponifying the ester, formed by process step a$_1$) or a$_2$), of the formula VI,

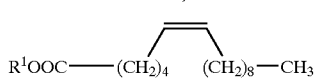

in which R$^1$ has the meaning given above.

Alkyl radicals for R$^1$ which may be mentioned are branched or unbranched C$_1$–C$_{12}$-alkyl chains, such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl and n-dodecyl. Preferred alkyl radicals are C$_1$–C$_4$-alkyl groups, particularly preferably methyl, ethyl, n-propyl and 1-methylethyl, very particularly preferably methyl and ethyl.

Aryl for R$^1$ is to be understood as meaning aromatic rings or ring systems having 6 to 18 carbon atoms in the ring system, for example phenyl or naphthyl, which may optionally be substituted by one or more radicals such as halogen, e.g. fluorine, chlorine or bromine, cyano, nitro, amino, C$_1$–C$_4$-alkylamino, C$_1$–C$_4$-dialkylamino, hydroxyl, C$_1$–C$_4$-alkyl, C$_1$–C$_4$-alkoxy or other radicals. Preference is given to phenyl, methoxyphenyl and naphthyl.

The term aryl for R$^2$ refers to customary aryl radicals occurring in phosphines and phosphonium salts, such as phenyl, toluene, naphthyl, in each case optionally substituted, preferably phenyl.

The radical X$^-$ is an anion equivalent of an inorganic or organic acid, preferably a strong inorganic or organic acid.

The expression strong acid includes hydrohalic acids (in particular hydrochloric acid and hydrobromic acid), sulfuric acid, phosphoric acid, sulfonic acids and other inorganic or organic acids with a comparable degree of dissociation. Strong organic acids in this connection are also to be understood as meaning C$_1$–C$_6$-alkanoic acids.

Particularly preference is given to anions of such acids, chosen from the group consisting of hydrochloric acid, hydrobromic acid, sulfuric acid, phosphoric acid, formic acid, acetic acid and sulfonic acid. Very particular preference is given to Cl$^-$, Br$^-$, C$_n$H$_{2n+1}$—SO$_3^-$ (where n=1–4), Ph—SO$_3^-$, p-Tol—SO$_3^-$ or CF$_3$—SO$_3^-$.

The invention provides, in particular, a process for the preparation of cis-6-hexadecenoic acid wherein, in process step a), a triphenylphosphonium salt of the formula II is reacted with decanal of the formula III.

A further preferred embodiment of the process involves using a triphenylphosphonium salt of the formula IIa,

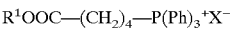

in which the substituents, independently of one another, have the following meanings:

R$^1$ is C$_1$–C$_4$-alkyl, in particular methyl, ethyl, n-propyl and 1-methylethyl;
Ph is phenyl;
X$^-$ is an anion equivalent of a strong inorganic or organic acid, in particular Cl$^-$, Br$^-$, C$_n$H$_{2n+1}$—SO$_3^-$ where n=1–4, Ph—SO$_3^-$, p-Tol—SO$_3^-$ or CF$_3$—SO$_3^-$.

The reaction of the phosphonium salts II to IV to give the cis-6-hexadecenoic esters of the formula VI can take place under the conditions customary for Wittig reactions.

The reaction in step a) usually takes place in temperatures between −30° C. and +50° C., preferably between −10 and +30° C., particularly preferably between +10° C. and +25° C.

In this connection, it is possible either to initially introduce both starting compounds (phosphonium salt and aldehyde) in the solvent and to add the base, or else to initially introduce a solution of the phosphonium salt, to add the base and only then to add a solution of the aldehyde.

Bases which can be used are all bases customary for Wittig condensations, e.g. alkali metal hydroxides, such as sodium hydroxide, potassium hydroxide or lithium hydroxide; alkali metal hydrides, such as sodium hydride or potassium hydride.

Also suitable as bases are organolithium compounds, such as, for example, n-butyllithium, tert-butyllithium, phenyllithium or alkali metal amides, such as lithium amide, potassium amide or sodium amide, lithium diisopropylamide and also alkali metal hexamethyldisilazides. Preferred bases used for the Wittig reaction according to the invention are sodium or potassium hexamethyldisilazide, and potassium amide or sodium amide.

The amount of base used is usually in the range from 0.8 to 5 mol, preferably 1 to 3 mol per mole of the phosphonium salt II or IV used.

Suitable solvents for the process step a) are, inter alia, aromatic hydrocarbons, such as toluene, xylene or benzene, cyclic or open-chain ethers, such as diethyl ether, diisopropyl ether, methyl tert-butyl ether, 1,4-dioxane or THF, and DMF or DMSO. Preferred solvents are toluene, THF and/or DMSO.

When conversion is complete, the reaction mixture is hydrolyzed, and the ester formed is removed from the aqueous solution by extraction.

The extractants used are advantageously hexane, heptane or ethyl acetate. It is, however, also possible to use all other water-immiscible organic solvents, such as ethers, aliphatic hydrocarbons, halogenated and aromatic hydrocarbons, for the extraction.

The solvents, in particular the DMF or DMSO, remain largely in the aqueous phase during this extraction and also retain the triphenylphosphine oxide, formed in the Wittig reaction, largely in the aqueous phase.

The process according to the invention is notable for the fact that the Wittig reaction in process step a) takes place with a Z/E selectivity greater than 90/10, preferably with a Z/E selectivity between 92/8 and 99/1, particularly preferably between 94/6 and 97/3.

The saponification in process step b) is usually carried out by initially introducing the cis-6-hexadecenoic ester in a $C_1$–$C_6$-alcohol, preferably ethanol, n-propanol, isopropanol or butanol, particularly preferably in ethanol, and adding a base, for example an aqueous or aqueous-alcoholic solution of an alkali metal or alkaline earth metal hydroxide, preferably an aqueous-ethanolic sodium hydroxide solution or potassium hydroxide solution.

The reaction temperatures in stage b) are in the range between 0° C. and the boiling temperature of the solvent, preferably between 10° C. and 100° C., particularly preferably in the range between 30° C. and 80° C.

The amount of catalyst used for the saponification of the ester is in the range between 0.01 and 5 mol %, preferably between 0.02 and 1 mol %, based on the starting material VI.

By reference to the examples below, the process according to the invention will be explained in more detail.

EXAMPLE 1

Reaction of ethyl 6-bromohexanoate with triphenylphosphine

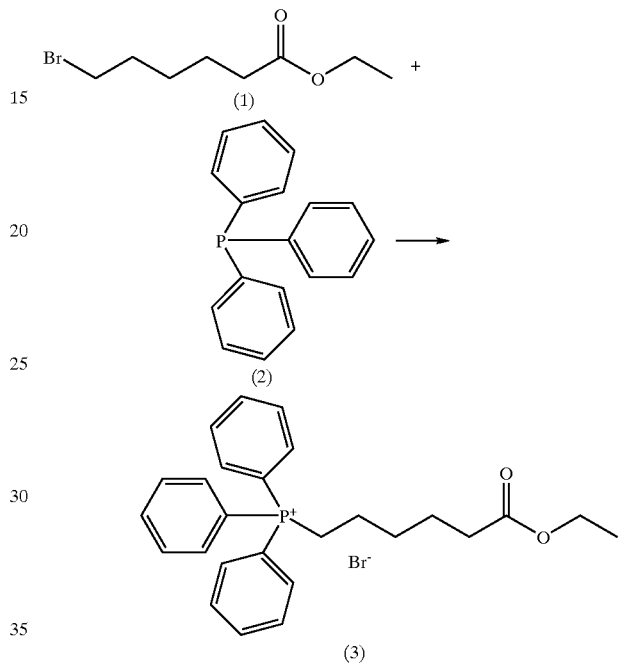

112.7 g (0.5 mol) of ethyl 6-bromohexanoate (1) (99% strength) were boiled under reflux together with 132.5 g (0.5 mol) of triphenylphosphine (2) (99% strength) in 600 ml of xylene in a 1 l two-necked flask for 6 hours. After the 6 hours, the mixture was cooled and the xylene was decanted off from the viscose product of value. The residue was boiled up with 2×600 ml of toluene and cooled, with the toluene being decanted off each time. The residual solvent was distilled off on a rotary evaporator to give 181.1 g of a glass-like, slightly yellowish crude product. According to $^1$H and $^{13}$C—NMR analyses, the product corresponded to compound (3). The yield was 76% of theory.

EXAMPLE 2

Reaction of the phosphonium salt with decanal to give ethyl cis-6-hexadecenoate

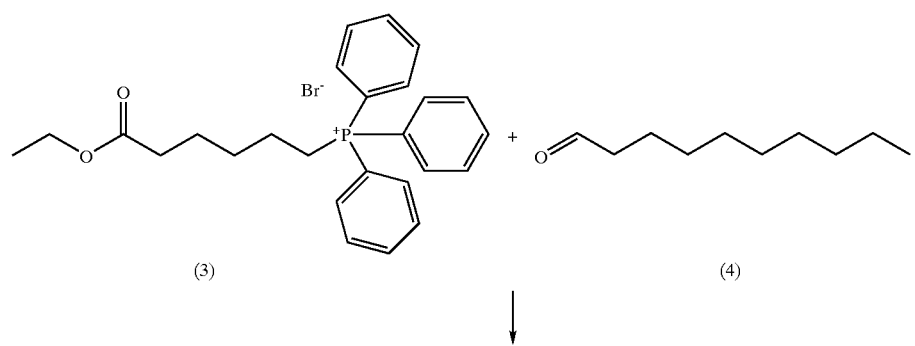

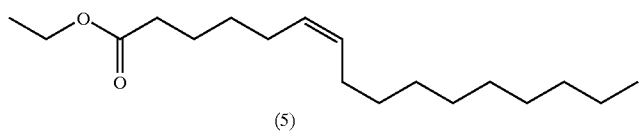

(5)

A 2 l four-necked flask fitted with paddle stirrer, thermometer and $N_2$ bubble counter was charged with 134.8 g (0.25 mol) of the phosphonium salt (3) obtained according to Example 1, together with 37.3 g (0.227 mol) of decanal (4) in 680 ml of DMSO. With stirring, a solution of 43.8 g (0.227 mol) of NaHMDS 95% strength and 226 ml of DMSO was added dropwise at from 20 to 25° C. over the course of 15 minutes. The mixture was then stirred for 24 hours at RT. The mixture was then introduced into 1100 ml of aqueous 1N HCl and 2000 ml of n-hexane. The water phase was once again extracted with 1000 ml of n-hexane. The combined organic phases were washed with 500 ml each of 5% strength aqueous $NaHCO_3$ solution and water, then dried with $Na_2SO_4$ and concentrated on a rotary evaporator. The residue was dissolved in 1000 ml of n-heptane and washed with 5×100 ml of water/methanol (1:1 v/v). The heptane phase was dried with $Na_2SO_4$ and then the heptane was distilled off on a rotary evaporator. The residue was transferred to a glass suction filter with silica gel and eluted with cyclohexane/ethyl acetate (2/1). The solvent was distilled off on a rotary evaporator, giving 38.9 g of residue. According to 1H and $^{13}C$—NMR analyses, the product corresponded to compound (5), 95% Z-isomer, 5% E-isomer. The yield was 35% of theory. The product was purified by distillation.

EXAMPLE 3
Saponification of the ethyl cis-6-hexadecenoate to give cis-6-hexadecenoic acid

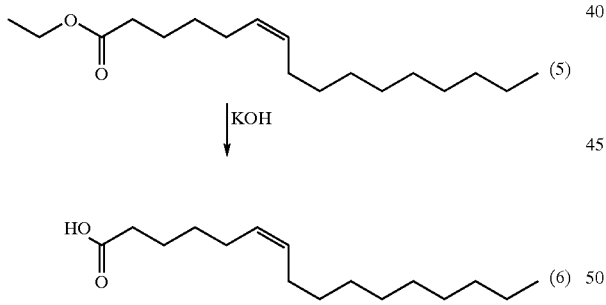

A 100 ml three-necked flask fitted with magnetic stirrer, reflux condenser and $N_2$ bubble counter was charged with 3.0 g of the crude ethyl cis-6-hexadecenoate (5) (6.16 mmol), together with 37.8 ml (37.8 mmol) of potassium hydroxide solution in ethanol c=1 mol/l and 18 ml of water. After the mixture had been refluxed for 2 hours, most of the solvent was stripped off on a rotary evaporator. 30 ml of ice water were added to the residue, which was extracted with 30 ml ethyl acetate. The organic phase was acidified with 4 ml of conc. hydrochloric acid. The organic phase was washed with 5 ml each of water and saturated sodium chloride solution and dried with $Na_2SO_4$, and the solvent was distilled off on a rotary evaporator. According to $^1H$ and $^{13}C$—NMR analyses, the resulting 2.59 g of yellowish substance corresponded to cis-6-hexadecenoic acid (6), 95% Z-isomer, 5% E-isomer. The yield was 95% of theory. Further purification of the cis-6-hexadecenoic acid was carried out by column chromatography. This gave a product with a chemical purity greater than 95%.

We claim:

1. A process for the preparation of cis-6-hexadecenoic acid of the formula I,

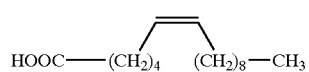

I which comprises reacting $a_1$) a triphenylphosphonium salt of the formula II,

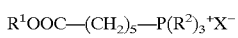

II in which the substituents, independently of one another, have the following meanings:
$R^1$ is $C_1$–$C_{12}$-alkyl, aryl;
$R^2$ is aryl and
$X^-$ is an anion equivalent of an inorganic or organic acid with decanal of the formula III

III in a Wittig reaction, or reacting $a_2$) a triphenylphosphonium salt of the formula IV,

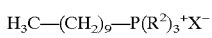

IV in which the substituents $R^2$ and $X^-$, independently of one another, have the meanings given above:

with an aldehyde of the formula V,

V in which $R^1$ has the meaning given above, in a Wittig reaction and b) saponifying the ester, formed by process step $a_1$) or $a_2$) of the formula VI,

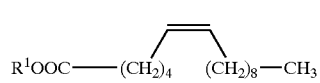

VI in which $R^1$ has the meaning given above, wherein the Wittig reaction in process step a) takes place with a Z/E selectivity greater than 90/10.

2. A process as claimed in claim 1 wherein, in process step a), a triphenylphosphonium salt of the formula II is reacted with decanal of the formula III.

3. A process as claimed in claim 2, wherein a triphenylphosphonium salt of the formula IIa is used

$$R^1OOC\text{—}(CH_2)_4\text{—}P(Ph)_3{}^+X^-\qquad\text{IIa}$$

in which the substituents, independently of one another, have the following meanings:

$R^1$ is $C_1$–$C_4$-alkyl;

Ph is phenyl;

$X^-$ is an anion equivalent of a strong inorganic or organic acid.

4. A process as claimed in claim 1, wherein $X^-$ is the anion equivalent of an acid chosen from the group consisting of hydrohalic acid, sulfuric acid, phosphoric acid, formic acid, acetic acid and sulfonic acid.

5. A process as claimed in claim 4, wherein $X^-$ is $Cl^-$, $Br^-$, $C_nH_{2n+1}$—$SO_3^-$ where n=1–4, Ph—$SO_3^-$, p-Tol—$SO_3^-$ or $CF_3$—$SO_3^-$.

* * * * *